United States Patent [19]

Tsubakimoto et al.

[11] 4,286,082

[45] Aug. 25, 1981

[54] ABSORBENT RESIN COMPOSITION AND PROCESS FOR PRODUCING SAME

[75] Inventors: Tsuneo Tsubakimoto; Tadao Shimomura, both of Toyonaka; Yoshio Irie, Ashiya; Yoshihiko Masuda, Suita, all of Japan

[73] Assignee: Nippon Shokubai Kagaku Kogyo & Co., Ltd., Osaka, Japan

[21] Appl. No.: 137,640

[22] Filed: Apr. 7, 1980

[30] Foreign Application Priority Data

Apr. 6, 1979 [JP] Japan .................................. 54/41125
Dec. 27, 1979 [JP] Japan ................................ 54/169368

[51] Int. Cl.$^3$ ................................................ C08F 2/18
[52] U.S. Cl. .................................... 526/240; 128/284; 128/285; 260/29.6 H; 260/29.6 TA; 260/42.29; 428/402; 428/407; 526/62; 526/210; 528/481; 528/503
[58] Field of Search ..................... 526/240; 260/42.29

[56] References Cited

U.S. PATENT DOCUMENTS

| | | | |
|---|---|---|---|
| 4,041,020 | 8/1977 | Gross | 526/240 |
| 4,093,776 | 6/1978 | Aoki et al. | 526/240 |

*Primary Examiner*—Stanford M. Levin
*Attorney, Agent, or Firm*—Sherman & Shalloway

[57] ABSTRACT

An absorbent resin composition obtained by copolymerizing in an aqueous solution a mixture of 100 parts by weight of an acrylate salt monomer (B) composed of 0 to 50 mol % of acrylic acid and 50 to 100 mol % of an alkali metal acrylate and 0.001 to 5 part by weight of a crosslinkable monomer (C) having 2 to 4 groups selected from the group consisting of $CH_2=CHCO-$, $CH_2=C(CH_3)CO-$ and $CH_2=CH-CH_2-$ in the molecule in the presence of at least one surface-active agent (A) selected from the group consisting of water-soluble surface-active agents and water-dispersible surface-active agents in the presence of a water-soluble radical polymerization initiator while maintaining the initial concentration of said mixture in the range of from 25% by weight to saturation, and then drying the resulting gel-like hydrous polymer under heat; and an absorbent resin composition obtained by pulverizing said absorbent resin composition to form a resin powder, and blending said resin powder with 0.01 to 10 parts by weight, per 100 parts by weight of said resin powder, of ultra-microscopic silica having a specific surface area, measured by the Brunauer-Emmett-Teller method, of at least 50 m$^2$/g and a particle diameter of not more than about 0.05 micron: and a process for producing the same.

18 Claims, No Drawings

ABSORBENT RESIN COMPOSITION AND PROCESS FOR PRODUCING SAME

This invention relates to an absorbent resin composition and a process for producing it. More specifically, the invention relates to an absorbent resin composition which, when in contact with aqueous fluids, absorbs the aqueous fluids to a high degree and maintains great fluid retention even under pressure; and a process for producing such an absorbent resin composition with high productivity without using an organic solvent.

In recent years, it has been attempted to use an absorbent resin as one constituent of sanitary materials absorbing body fluids, such as sanitary napkins or paper diapers. Such an absorbent resin includes, for example, the neutralization products of starch-acrylic acid graft copolymers (U.S. Pat. No. 4,076,663), which, however, pose the problems that since it is necessary to neutralize high-viscosity substances or perform polymerization in organic solvents, productivity will be low, and that when the organic solvent is used, there will be a danger of explosion or fire and the safety of the operator will be endangered.

Potassium polyacrylate crosslinked with polyvalent metal ions (U.S. Pat. No. 4,090,013) and spontaneously crosslinked sodium polyacrylate obtained by water-in-oil suspension polymerization (U.S. Pat. No. 4,093,776) are also known as absorbent resins. However, they both use organic solvents during production, thus posing the aforementioned problems and involving the defects of high water-solubles contents and low water-absorbing property. Hence, these absorbent resins are problematical in that when contacted with catamenial blood, urine or other body fluids, they have low initial absorption rates and less saturated absorptions, and become sticky. Also, their high water-solubles contents render these absorbent resins questionable in the safety of the skin and mucosae of the human body. When powders of the absorbent resins are fabricated into absorbent sheets, a uniform distribution of the powder does not take place because the powder absorbs moisture and loses its fluidity, and the absorbed moisture causes the powder to stick to the sheet-fabricating machine. Another drawback is that when in contact with an aqueous fluid, the powder of the absorbent resin tends to form fish-eyes, thereby extremely lowering the absorption capacity in the initial stage.

The object of the present invention is to solve the above-mentioned various problems facing the conventional absorbent resins.

The present inventors have found that said object of the present invention can be attained by an absorbent resin composition obtained by copolymerizing in an aqueous solution a mixture of 100 parts by weight of an acrylate salt monomer (B) composed of 0 to 50 mol% of acrylic acid and 50 to 100 mol% of an alkali metal acrylate and 0.001 to 5 parts by weight of a crosslinkable monomer (C) having 2 to 4 groups selected from the group consisting of $CH_2=CHCO-$, $CH_2=C(CH_3)CO-$ and $CH_2=CH-CH_2-$ in the molecule in the presence of at least one surface-active agent (A) selected from the group consisting of water-soluble surface-active agents and water-dispersible surface-active agents in the presence of a water-soluble radical polymerization initiator while maintaining the initial concentration of said mixture in the range of from 25% by weight to saturation, and then drying the resulting gel-like hydrous polymer under heat [hereinafter referred to as absorbent resin composition (I)]; and an absorbent resin composition obtained by pulverizing said absorbent resin composition (I) to form a resin powder (D), and blending said resin powder (D) with 0.01 to 10 parts by weight, per 100 parts by weight of said resin powder (D), of ultramicroscopic silica (E) having a specific surface area, measured by the Brunauer-Emmett-Teller method, of at least about 50 $m^2/g$, and a particle diameter of not more than about 0.05$\mu$ [hereinafter referred to as absorbent resin composition (II)].

The surface-active agent (A) used in the present invention is at least one member selected from the group consisting of water-soluble surface-active agents and water-dispersible surface-active agents. Such surface active agent (A) may be at least one member selected from nonionic surface-active agents or anionic surface-active agents such as polyoxyethylene alkyl ethers [alkyl=lauryl, cetyl, stearyl or oleyl; HLB (hydrophile lipophile balance) value=9.4–17.1], polyoxyethylene secondary alkyl ethers (alkyl=$C_{12}$-$C_{14}$ hydrocarbon; HLB value=7.9–14.5), polyoxyethylene alkylphenol ethers (alkyl=octyl or nonyl; HLB value=7.8–18.9), sorbitan monolaurate (HLB value=8.0), polyoxyethylene sorbitan fatty acid esters (fatty acid ester=monolaurate, monostearate, monooleate, or monopalmitate; HLB value=9.6–16.7), polyoxyethylene fatty acid esters (fatty acid ester=monolaurate, monostearate or monooleate; HLB value=13.4–19.1), sugar fatty acid esters (HLB value=8.0–15.0), polyoxyethylene-polyoxypropylene glycol block copolymer, sodium dodecylbenzene sulfonate, and sodium alkyl sulfates (alkyl=$C_{12}$-$C_{14}$ hydrocarbon). Of these surface-active agents, the nonionic surface-active agents having an HLB of 7 to 20, preferably 8 to 17, are desirable in the present invention.

The amount of the surface-active agent (A) used is 0.01 to 10 parts by weight, preferably 0.05 to 5 parts by weight, more preferably 0.1 to 2 parts by weight, per 100 parts by weight of the acrylate salt monomer (B). When the amount of the surface-active agent (A) used is less than said lower limit, compatibility between an aqueous solution of the acrylate salt monomer (B) and the crosslinkable monomer (C) is poor, thus failing to give a uniform crosslinked polymer. In this case, moreover, the resulting gel-like hydrous polymer has great stickiness, thus making it difficult to release the polymer from the polymerization vessel and making poor its workability during cutting or molding by, say, an extruder. Further, an absorbent resin composition obtained by heat-drying the gel-like hydrous polymer absorbs an aqueous fluid at a low initial absorption rate. When the amount of the surface-active agent (A) used exceeds said upper limit, the molecular weight of a crosslinked polymer to be obtained decreases owing to chain transfer to the surface-active agent (A) during the polymerization, thus making the resulting gel-like hydrous polymer soft and difficult to handle. Also, an absorbent resin composition obtained by heat-drying the polymer is low in absorption capacity when in contact with an aqueous fluid.

The surface-active agent (A) is perfectly dissolved or finely emulsified and dispersed in an aqueous solution of the acrylate salt monomer (B) before polymerization is initiated. At the time of polymerization, the surface-active agent (A) renders the crosslinkable monomer (C), which has poor compatibility with the aqueous solution of the acrylate salt monomer (B), soluble in the aqueous solution of the acrylate salt monomer (B), and enhances the copolymerizability of the acrylate salt monomer (B) and the crosslinkable monomer (C), thereby acting to perform uniform crosslinking. As the polymerization proceeds, the surface-active agent (A) separates in the resulting gel-like hydrous polymer, turning into a milky-white uniform dispersion. As a result, the resulting gel-like hydrous polymer contains in its surface and inside fine particles or fine liquid drops of the surface-active agent (A). This will diminish the adhesion of the gel-like hydrous polymer to the polymerization vessel, greatly improving its releasability. When the gel-like hydrous polymer is brought into contact with a metallic cutter, kneader, screw or nozzle for cutting or shaping, or a new cut surface is formed by cutting, the polymer always has good releasability because it contains fine particles or fine liquid drops of the surface-active agent (A) uniformly present in the inside.

The acrylate salt monomer (B) used in the present invention is composed of 0 to 50 mol% of acrylic acid and 50 to 100 mol% of an alkali metal acrylate. If the proportion of the alkali metal acrylate is less than 50 mol%, the resulting gel-like hydrous polymer is highly sticky and poorly releasable from the polymerization vessel, thus making its handling difficult at the time of cutting or shaping by an extruder, for example. In the acrylate salt monomer (B) in the present invention, the proportion of the alkali metal acrylate may be 100 mol%. If necessary, a base, such as an alkali metal hydroxide, for neutralizing acrylic acid may be used in a proportion of at least one mole per mol of the acrylic acid. The polymerizability of an aqueous solution of the acrylate salt monomer is better as the ratio of neutralization of acrylic acid becomes higher. However, if the pH of the resulting crosslinked polymer being contacted with or dispersed in an aqueous fluid to be absorbed is to be maintained in a range safe for the skin of the human body, it is desirable to set the proportion of the alkali metal acrylate in the acrylate salt monomer (B) at 60 to 90 mol%, preferably 65 to 80 mol%.

The acrylic acid used in the present invention may be a marketed one. If desired, part of the acrylic acid may be replaced with other water-soluble polymerizable carboxylic acid such as methacrylic acid.

Examples of the alkali metal are those widely used, such as lithium, sodium or potassium. Sodium, in particular, is preferred in safety, in view of the fact that sodium polyacrylate is accepted as a food additive in Japan.

The crosslinkable monomer (C) for use in the present invention is that having in one molecule 2 to 4 groups selected from the group consisting of $CH_2=CHCO-$, $CH_2=C(CH_3)CO-$ and $CH_2=CH-CH_2-$. Preferred as such cross-linkable monomer (C) is at least one member selected from the group consisting of diacrylates and dimethacrylates of ethylene glycol, diethylene glycol, triethylene glycol, propylene glycol, 1,4-butanediol, 1,5-pentanediol, 1,6-hexanediol, neopentyl glycol, trimethylolpropane and pentaerythritol; triacrylates and trimethacrylates of trimethylolpropane and pentaerythritol; tetraacrylate and tetramethacrylate of pentaerythritol; N,N'-methylenebisacrylamide; N,N'-methylenebismethacrylamide; and triallyl isocyanurate. Of these compounds, N,N'-methylenebisacrylamide or trimethylolpropane triacrylate is particularly preferred. The amount of the crosslinkable monomer (C) is 0.001 to 5 parts by weight, preferably 0.01 to 2 parts by weight, more preferably 0.02 to 1 part by weight, per 100 parts by weight of the acrylate salt monomer (B). If the amount of the crosslinkable monomer (C) used is more than 5 parts by weight, the resulting product has too high a crosslinking density and its absorption capacity rather lowers. If that amount is less than 0.001 part by weight, the product has too low a crosslinking density, and when contacted with a fluid to be absorbed, it becomes sticky and its initial absorption rate lowers.

As mentioned above, the crosslinkable monomer (C) is used in a comparatively small amount of 0.001 to 5 parts by weight per 100 parts by weight of the acrylate salt monomer (B) in the present invention. Nevertheless, the crosslinkable monomer (C) copolymerizes with the acrylate salt monomer (B) uniformly and efficiently thanks to the joint use of the surface-active agent (A) and the copolymerization in a high-concentration aqueous solution, whereby a crosslinked polymer of a uniform crosslinking structure is afforded.

For the aqueous-solution copolymerization according to the present invention, the acrylate salt monomer (B), the crosslinkable monomer (C) and the surface-active agent (A) are mixed in a customary manner prior to the copolymerization. They may be mixed in any sequence. If desired, other ingredients may be added to the mixture. Examples of such other ingredients include polyhydric alcohols such as diethylene glycol or glycerine. If such polyhydric alcohol is jointly used when the proportion of the alkali metal acrylate in the acrylate salt monomer (B) is less than 100 mol% (namely, when a carboxyl group based on acrylic acid is present) in the present invention, crosslinking due to the reaction between the carboxyl group in the resulting gel-like hydrous polymer and the polyhydric alcohol also takes place during the step of heat-drying the polymer. In this way, a crosslinkage from the crosslinkable monomer (C) and a crosslinkage from the polyhydric alcohol can be co-present in the resulting crosslinked polymer.

The preferred method of the aqueous-solution polymerization adopted in the present invention is the bulk polymerization or cast polymerization, in an atmosphere of nitrogen, of an aqueous solution or aqueous dispersion in which the acrylate salt monomer (B), the crosslinkable monomer (C), the surface-active agent (A), and a water-soluble radical polymerization initiator are uniformly mixed and the mixture of the acrylate salt monomer (B) and the crosslinkable monomer (C) is contained in a concentration of from 25% by weight to saturation, preferably from 25 to 50% by weight, more preferably from 30 to 45% by weight. To remove heat generated by the polymerization and facilitate the control of the reaction temperature, it is preferred to effect the polymerization in a closed vessel having a relatively large heat transfer area. For this aqueous-solution polymerization, a polymerization vessel as described in Japanese Patent Publication No. 42466/73, for example, is preferred. If the initial concentration of the monomers is lower than 25% by weight, it is hard for the crosslinked polymer to have a high molecular weight, and thus, the resulting hydrous polymer is a soft gel-like polymer which is hard to handle.

The initiator used in the aqueous-solution polymerization may be an ordinary water-soluble radical polymerization initiator. For example, ammonium persulfate, potassium persulfate, and hydrogen peroxide can be cited. There are also usable redox type initiators consisting of said initiators combined with reducing agents such as sodium hydrogensulfite, L-ascorbic acid or ferrous salts.

The polymerization temperature for the polymerization is preferably a relatively low temperature which increases the molecular weight of the resulting crosslinked polymer. For the completion of the polymerization, the preferred temperature ranges from 10° C. to 80° C.

To obtain the absorbent resin composition (I) by drying under heat a gel-like hydrous polymer comprising the crosslinked polymer that has been formed by the aqueous-solution copolymerization, it is desirable to dry the gel-like hydrous polymer at as high an efficiency and in as short a time as possible in order to prevent the deterioration of the polymer due to excessive heat. A desirable method of such drying comprises heating the gel-like hydrous polymer by hot air at a temperature of 100° to 230° C., preferably 120° to 200° C. after cutting or extruding the polymer to give it a surface area, per unit volume, of at least 9 cm$^2$/cm$^3$.

If a mixed aqueous solution of the acrylate salt monomer (B) and the crosslinkable monomer (C) were polymerized in the absence of the surface-active agent (A) and then the surface-active agent (A) were added to the resulting gel-like hydrous polymer, unlike the present invention, it would be impossible to effect a uniform copolymeric crosslinking of the acrylate salt monomer (B) and the crosslinkable monomer (C). Nor would such method enable the surface-active agent (A) to be distributed uniformly inside of the gel-like hydrous polymer; hence, it would be impossible to prevent the adhesion of the polymer during cutting or extrusion. Even if the cross-linked polymer so obtained were made into a powder, the surface-active agent (A) would not be distributed uniformly in the powder. Such powder is not expected to be free from generating dust or to prevent the formation of fish-eyes when contacted with an aqueous fluid. On the other hand, if an aqueous solution of the acrylate salt monomer (B) containing the crosslinkable monomer (C) and the surface-active agent (A) were subjected to a water-in-oil suspension polymerization in an organic solvent, the crosslinkable monomer (C) would be extracted into the organic solvent side and effective copolymeric crosslinking could not take place; therefore, the resulting polymer would contain high water-solubles content and have a low water-absorbing property.

The absorbent resin composition (I) obtained by drying the gel-like hydrous polymer under heat is suitably pulverized into coarse particles, granules or a powder for application to the desired uses. The way of pulverization is not critical, and a known method can be employed suitably. According to the present invention, the absorbent resin composition (I) formed by drying the gel-like hydrous polymer under heat has fine particles or fine liquid drops of the surface-active agent (A) uniformly dispersed in its surface and inside, and hence, can be easily pulverized in a short time. Even if a fine powder were formed in this pulverization step, the fine particles or fine liquid drops of the surface-active agent (A) uniformly dispersed in the surface and inside of the fine powder would render it apt to slightly agglomerate and would not cause it to raise dust.

The absorbent resin composition (I) has excellent performance compared with conventional known absorbent resins. In detail, the composition (I) has a high degree of polymerization because it has been prepared from the gel-like hydrous polymer formed by copolymerization in an aqueous solution in a relatively high concentration. Moreover, it is efficiently and uniformly crosslinked by copolymerizing the acrylate salt monomer (B) and the crosslinkable monomer (C) in the presence of the surface-active agent (A). Therefore, the absorbent resin composition (I) has a very low water-solubles content, and thus, is less sticky when in contact with an aqueous fluid and has a large amount of saturated absorption. The absorbent resin composition (I) contains fine particles or fine liquid drops of the surface-active agent (A) uniformly dispersed in the surface and inside thereof, thus having a high initial absorption rate and scarcely forming fish-eyes. Little content of water-solubles makes the composition (I) less irritant to the skin of the human body. Further, the pH of the system of the absorbent resin composition (I) in contact with an aqueous fluid can be adjusted to a range safe for the skin by suitably selecting the proportions of the acrylic acid and alkali metal acrylate in the acrylate salt monomer (B) from the aforementioned range.

In addition, the absorbent resin composition (I) is very high in heat resistance, and when it is fabricated into an absorbent sheet or the like by heating or other method, its absorption capacity never deteriorates and its degeneration never occurs. And the absorbent resin composition (I) is completely free from impurities such as organic solvents or inorganic salts.

In a preferred embodiment of the present invention, the absorbent resin composition (I) having such excellent properties is pulverized, and specific ultramicroscopic silica (E) is blended with the resulting resin powder (D), thereby to prepare the absorbent resin composition (II). The absorbent resin composition (II) causes little reduction in fluidity and little caking by absorbing moisture, and has excellent workability when handled, while maintaining the superior properties that the absorbent resin composition (I) possesses.

The ultramicroscopic silica (E) has a specific surface area, measured by the Brunauer-Emmett-Teller method, of at least about 50 m$^2$/g and a particle diameter of not more than about 0.05$\mu$. Any silica having said specific surface area and particle diameter may be used even when part of or all of the silanol groups in the surface of the silica particles have been rendered hydrophobic. Silica having a specific surface area of less than about 50 m$^2$/g or a particle diameter in excess of about 0.05$\mu$ is insufficient in the effects of preventing the lowering of fluidity or caking.

The amount of the ultramicroscopic silica (E) used is 0.01 to 10 parts by weight per 100 parts by weight of the resin powder (D) (a powder of the absorbent resin composition (I)). Preferably, the amount is 0.05 to 5 parts by weight, more preferably 0.1 to 2 parts by weight.

The way of blending the resin powder (D) and the ultramicroscopic silica (E) for the formation of the absorbent resin composition (II) is not critical, and an ordinary mixing method and an ordinary mixing device may be used for this purpose.

The absorbent resin composition (I) and the absorbent resin composition (II) according to the present invention have the aforementioned excellent properties, are producible commercially with good productivity, and can be supplied for relatively low price. When they are used as absorbents of sanitary napkins or paper diapers, their absorption capacity per unit price is remarkably high.

The absorbent resin compositions (I) and (II) of the present invention find wide application. For example, when used as absorbents of sanitary napkins or paper diapers, they quickly absorb large amounts of catamenial blood, urine or other body fluids, and even under pressure, retain the absorbed fluids. Therefore, they are felt comfortable to use and withstand a long period of use. For such use, said absorbent resin compositions may be scattered unchanged between substrates making up sanitary napkins or paper diapers, such as paper, pulp or nonwoven fabric, or may be shaped into sheets. The methods of sheeting include: a method comprising stacking plural layers of paper or nonwoven fabric, scattering a powder of said absorbent resin composition between said layers to form a sandwich, and press-bonding the constituents of the sandwich with an emboss roll; a method comprising mixing a powder of said absorbent resin composition with fluff pulp pulverized in the form of a powder or short fiber, and press-bonding the mixture; and a method comprising further interposing said press-bonded mixture between sheets of paper or nonwoven fabric to form a sandwich. In these methods, water, steam, a low-temperature-melting thermoplastic resin or an adhesive resin may also be used as a binder.

The present invention will be illustrated in more detail by way of Examples, but it is to be noted that the invention is not limited to the Examples.

EXAMPLE 1

Four openable air-tight vessels, of which the inner surface was lined with polytetrafluoroethylene resin, made of SUS 304 and having a capacity of 300 mm×300 mm×50 mm were charged with 4,000 g of an aqueous solution (monomer concentration: 43 weight%) containing an acrylate salt monomer (B) consisting of 75 mol% of sodium acrylate and 25 mol% of acrylic acid and various kinds of the crosslinkable monomers (C) and the surface-active agents (A) in amounts indicated in Table 1. The solution was heated to 40° C. in an atmosphere of nitrogen, and then, 0.6 g of ammonium persulfate and 0.2 g of sodium hydrogen sulfite were added and homogeneously dissolved in it. The polymerization proceeded gently, and the solution turned into a turbid gel with generation of heat. The temperature of the reaction system reached 55°–80° C. in the course of 2–5 hours after initiation of polymerization.

After 7 hours from the initiation of polymerization, the vessels were opened, and the gel-like hydrous polymers formed were collected. Any of the gel-like hydrous polymers could be very easily released from the vessels. These collected polymers were cut in 1 cm square by a steel cutter. In this cutting process, no adhesion to the cutter was observed, and the operability was satisfactory.

Then, using a single-screw extruder (screw diameter: 30 mm, L/D=17, the revolution speed of screw: 45 rpm), of which the contact part was made of SUS 316, the 1 cm square cut polymers were extruded through a multi-nozzle die having nozzles with 1.5 mm diameter to form string-like gels having about 2 mm diameter. The string-like gel had a surface area, per unit volume, of about 20 $cm^2/cm^3$. The resulting string-like gels were dried at 180° C. for 90 minutes in a hot air dryer to afford absorbent resin compositions (1) to (4).

The absorbent resin compositions (1) to (4) thus prepared were pulverized to powders by a vibrating mill. The respective powders were put uniformly each in an amount of 0.2 g in tea-bag type bags (40 mm×150 mm) made of nonwoven fabric. The bags were immersed in a 0.9% saline solution, and weighed after 3 minutes and 5 minutes, respectively. The absorbency of the absorbent resin compositions were calculated in accordance with the following equation, in which the blank is the weight of only the tea-bag type bag after absorption.

$$\text{Absorbency} = \frac{\text{Weight after absorption (g)} - \text{Blank (g)}}{\text{Weight of powder (g)}}$$

Further, 20 g of each of the resulting powders was charged into a glass sampling bottle having a capacity of 100 ml, and the generation of dust of the compositions after 10 seconds shaking of the bottle was observed.

Next, the absorbent resin compositions (1)–(4) (0.5 g) were respectively dispersed in 1000 ml of deionized water. After stirring for 30 minutes, the dispersions were filtered with a filter (No. 6 filter paper made by Toyo Roshi Co., Ltd., Japan), and the solids content of the filtrates was measured. The water-solubles content of the absorbent resin compositions was determined in accordance with the following equation.

$$\text{Water-solubles content (weight \%)} = \frac{\text{Weight of filtrate} \times \text{Solids content of filtrate (weight \%)}}{0.5}$$

Further, the pH of a 1% by weight aqueous dispersions containing these absorbent resin compositions was measured.

The results are shown in Table 1.

EXAMPLE 2

Absorbent resin compositions (5)–(12) were prepared by repeating the same procedure as in Example 1, except that the surface-active agent (A), the acrylate salt monomer (B), the crosslinkable monomers (C), and the monomer concentration of the aqueous solution were changed as indicated in Table 1.

In the same way as in Example 1, the absorbency, the water-solubles content, the pH of 1% by weight aqueous dispersion, and the generation of dust of these absorbent resin compositions (5)–(12) were determined, and the results are shown in Table 1. The releasability of the gel-like hydrous polymers from the polymerization vessel are also shown in Table 1.

EXAMPLE 3

The absorbent resin composition (13) was prepared by the same procedure as in Example 1 except that an acrylate salt monomer (B) consisting of 75 mol% of potassium acrylate and 25 mol% of acrylic acid was used.

In respect of the absorbent resin composition (13), the absorbency, the water-solubles content, the pH of 1% by weight aqueous dispersion, and the generation of dust were determined in the same way as in Example 1, and the results are shown in Table 1. The releasability of the gel-like hydrous polymer from the polymerization vessel was also shown in Table 1.

COMPARATIVE EXAMPLE 1

The procedure for the preparation of the absorbent resin composition (3) in Example 1 was repeated, except that the crosslinkable monomer (C) was not used, to obtain a polymer (hereinafter called the comparative resin composition (1)). The properties of the comparative resin composition (1) were determined in the same way as in Example 1, and the results are shown in Table 1. The powder of this comparative resin composition (1) has a high water-solubles content, and therefore, was not suitable as an absorbent.

COMPARATIVE EXAMPLE 2

The polymerization was conducted in the same manner as in the preparation of the absorbent resin composition (1) in Example 1 except that the surface-active agent (A) was not used. In this case, the acrylate salt monomer (B) and the crosslinkable monomer (C) did not form a homogeneous aqueous solution or aqueous dispersion, and the crosslinkable monomer (C) tended to separate. And the gel-like hydrous polymer obtained by polymerization was highly sticky to the reaction vessel, with the consequence that it was difficult to release the polymer from the vessel. The resulting comparative resin composition (2) generated much dust when it was pulverized.

COMPARATIVE EXAMPLE 3

The polymerization was performed in the same manner as in the preparation of the absorbent resin composition (3) in Example 1 except that the proportion of sodium acrylate in the acrylate salt monomer (B) was 40 mol%. The polymerization abruptly started after a long induction period. The resulting gel-like hydrous polymer was soft, and showed high stickiness. Consequently, the releasability from the vessel was not good. The comparative resin composition (3) obtained from the above gel-like hydrous polymer in the same manner as in Example 1 had a low absorbency and a low pH of 1% by weight aqueous dispersion, as seen from the results in Table 1.

COMPARATIVE EXAMPLE 4

The polymerization was conducted in the same manner as in the preparation of the absorbent resin composition (3) in Example 1 except that the concentration of a monomer mixture of the acrylate salt monomer (B) and the crosslinkable monomer (C) in an aqueous solution was changed to 15 weight %.

The gel-like hydrous polymer obtained by polymerization was extremely soft, and its stickiness was so high that the polymer could not be easily released from the polymerization vessel. A comparative resin composition (4) was prepared from the above gel-like hydrous polymer in the same way as in Example 1, but its water-solubles content was high and its absorbency was poor, as shown in Table 1.

COMPARATIVE EXAMPLE 5

The absorbency, the water-solubles content, the pH of 1% by weight aqueous dispersion, and the generation of dust in respect of a commercially available sodium salt of starch-acrylic acid graft copolymer as the comparative resin composition (5) were determined in the same way as in Example 1. As apparent from the results shown in Table 1, this comparative resin composition had a high water-solubles content, and its absorbency was low.

COMPARATIVE EXAMPLE 6

A separable flask having an inner capacity of 1 liter was charged with 300 ml of n-hexane, 100 g of an aqueous solution (monomer concentration: 40%) containing an acrylate salt monomer (B) consisting of 75 mol% of sodium acrylate and 25 mol% of acrylic acid, 0.4 g of trimethylolpropane triacrylate, 2 g of sorbitan monostearate and 0.05 g of ammonium persulfate. The mixture was suspended in water-in-oil suspension and was heated to 62° C. under an atmosphere of nitrogen with stirring to effect a water-in-oil suspension polymerization. After 6 hours from the initiation of polymerization, the suspension formed was filtered, and washed with n-hexane, followed by drying under reduced pressure, to obtain a crosslinked product of sodium polyacrylate (comparative resin composition (6)). The properties of this comparative resin composition were measured in the same way as in Example 1. As shown in Table 1, this composition had a high water-solubles content and a low absorbency, and generated a considerable amount of dust.

TABLE 1

| | | Alkali metal acrylate in acrylate salt monomer (B) (mol %) | Monomer concentration of aqueous solution of acrylate salt monomer (B) (wt. %) | Crosslinkable monomer (C) Kind | Amounts (Note 1) | Surface-active agent (A) Kind (Note 2) | Amounts (Note 1) | Releasability (Note 3) | Absorbency (0.9 saline solution) 3 minutes | 5 minutes | Water-solubles content (wt. %) | pH (1 wt. % solution) | Generation of dust (Note 4) |
|---|---|---|---|---|---|---|---|---|---|---|---|---|---|
| Example 1 | Absorbent resin composition (1) | 75 | 43 | Trimethylolpropane triacrylate | 0.1 | Softanol 70 | 2 | ◎ | 42 | 42 | 6.7 | 7.0 | ◎ |
| | Absorbent resin composition (2) | 75 | 43 | N,N-methylenebis acrylamide | 0.1 | Span 20 | 0.5 | ◎ | 42 | 42 | 5.3 | 7.0 | ○ |
| | Absorbent resin composition (3) | 75 | 43 | Pentaerythritol triacrylate | 0.1 | Tween 60 | 1 | ◎ | 34 | 35 | 7.2 | 7.0 | ◎ |
| | Absorbent resin composition (4) | 75 | 43 | Ethylene glycol dimethacrylate | 0.4 | Neopelex 05 | 1 | ○ | 36 | 41 | 3.9 | 7.0 | ◎ |
| Example 2 | Absorbent resin composition (5) | 70 | 41 | Triethylene glycol diacrylate | 0.2 | Nonypol 100 | 1 | ◎ | 47 | 48 | 2.7 | 6.7 | ◎ |
| | Absorbent resin composition (6) | 70 | 41 | 1,4-Butanediol diacrylate | 0.2 | Softanol 70 | 1 | ◎ | 41 | 41 | 4.1 | 6.7 | ◎ |
| | Absorbent resin composition (7) | 80 | 37 | 1,6-Hexanediol diacrylate | 0.2 | Softanol 70 | 3 | ◎ | 35 | 41 | 6.1 | 7.3 | ○ |
| | Absorbent resin composition (8) | 75 | 40 | Trimethylolpropane trimethacrylate | 0.3 | Span 20 | 0.2 | ◎ | 42 | 42 | 5.2 | 7.0 | ◎ |
| | Absorbent resin composition (9) | 75 | 40 | Pentaerythritol tetraacrylate | 0.1 | Tween 60 | 1 | ◎ | 41 | 42 | 7.3 | 7.0 | ◎ |
| | Absorbent resin composition (10) | 75 | 40 | Neopentyl glycol diacrylate | 0.1 | Softanol 70 | 1 | ◎ | 40 | 43 | 7.9 | 7.0 | ◎ |
| | Absorbent resin composition (11) | 75 | 40 | Pentaerythritol diacrylate | 0.1 | Softanol 70 | 1 | ◎ | 35 | 42 | 7.4 | 7.0 | ◎ |
| | Absorbent resin composition (12) | 75 | 40 | Triallyl isocyanurate | 0.1 | Softanol 70 | 1 | ◎ | 35 | 42 | 8.7 | 7.0 | ◎ |
| Example 3 | Absorbent resin composition (13) | 75 | 43 | Trimethylolpropane triacrylate | 0.1 | Softanol 70 | 2 | ◎ | 40 | 42 | 7.0 | 7.0 | ◎ |
| Comparative Example 1 | Comparative resin composition (1) | 75 | 43 | not used | — | Tween 60 | 1 | ◎ | 15 | 23 | 59 | 7.0 | ◎ |
| Comparative Example 2 | Comparative resin composition 2 | 75 | 43 | Trimethylol propane triacrylate | 0.1 | — | — | × | 30 | 33 | 15 | 7.0 | × |
| Comparative Example 3 | Comparative resin composition (3) | 40 | 43 | Pentaerythritol trimethacrylate | 0.1 | Tween 60 | 1 | × | 24 | 26 | 6.3 | 5.2 | ◎ |
| Comparative Example 4 | Comparative resin composition 4 | 75 | 15 | Pentaerythritol trimethacrylate | 0.1 | Tween 60 | 1 | × | 18 | 32 | 52 | 7.0 | ○ |
| Comparative Example 5 | Comparative resin composition 5 | Commercially available sodium salt of starch-acrylic acid graft copolymer. | | | | | | — | 25 | 25 | 30 | 7.1 | ○ |
| Comparative Example 6 | Comparative resin composition 6 | Crosslinked product of sodium polyacrylate produced by | | | | | | — | 17 | 24 | 45 | 7.0 | × |

TABLE 1-continued

| | Alkali metal acrylate salt in acrylate salt monomer (B) (mol %) | Monomer concentration of aqueous solution of acrylate salt monomer (B) (wt. %) | Crosslinkable monomer (C) Kind | Amounts (Note 1) | Surface-active agent (A) Kind (Note 2) | Amounts (Note 1) | Releasability (Note 3) | Absorbency (0.9 saline solution) 3 minutes / 5 minutes | Water-solubles content (wt. %) | pH (1 wt. % solution) | Generation of dust (Note 4) |
|---|---|---|---|---|---|---|---|---|---|---|---|
| Example 6 | composition (6) water-in-oil suspension polymerization. | | | | | | | | | | |

(Note 1)
The amounts added are based on 100 parts of acrylate salt monomer (B).
(Note 2)
"Softanol 70": polyoxyethylene secondary alkylether (HLB 12.1), a product of Nippon Shokubai Kagaku Kogyo Co., Ltd.
"Span 20": sorbitan monolaurate (HLB 8.0), a product of Kao-Atlas Co., Ltd.
"Tween 60": polyoxyethylene sorbitan monostearate (HLB 14.9), a product of Kao-Atlas Co., Ltd.
"Neoplex 05": sodium dodecylbenzene sulfonate, a product of Kao-Atlas Co., Ltd.
"Nonypol 100": polyoxyethylene nonylphenyl ether (HLB 13.3), a product of Sanyo Chemical Industries, Ltd.
(Note 3)
Releasability shows the degree of the release of the polymer from the polymerization vessel.
⊚ Extremely good
○ Good
X Poor
(Note 4)
Generation of dust shows the generation of dust of the powders in a glass bottle.
⊚ No generation of dust
○ Slight generation of dust
X Considerable generation of dust As apparent from the results shown in Table 1, the absorbent resin compositions of the present invention have excellent absorbency and an extremely low water-solubles content. And the swollen gel of the absorbent resin compositions formed by absorbing a liquid to be absorbed was not sticky, and the generation of dust was hardly observed. The pH of these absorbent resin compositions in a 1% by weight aqueous dispersion was in a range of 6.7–7.3 in all cases, while that of a commercially available high-molecular sodium polyacrylate in 1% by weight aqueous solution was 9.6. This means the absorbent resin compositions of this invention had safe pH values to the skin of the human body.

EXAMPLE 4

Absorbent resin compositions (14)–(17) were prepared by blending 1 Kg of powder of the absorbent resin composition (6) obtained in Example 2 with ultramicroscopic silica (E) in the kinds and the amounts indicated in Table 2, using a V-type blender having a capacity of 5 liters (the revolution speed: 10 rpm, time: 10 minutes). One gram of each of these compositions (14)–(17) was placed in a laboratory dish having a diameter of 100 mm. The compositions were allowed to stand under condition of 20° C. and 65% RH, and the times until the fluidity of the powders disappeared were measured. This measurement was also conducted in respect of the absorbent resin composition (6) not containing the ultramicroscopic silica (E). Again, the absorbency of the absorbent resin compositions (14)–(17) in 0.9% saline solution was determined in the same way as in Example 1, and the results are shown in Table 2.

TABLE 2

| Absorbent resin composition | Ultramicroscopic silica (E) Kind | Amount (g) | Time until the fluidity disappeared (hr.) | Absorbency in 0.9% saline solution (times) After 3 min. | After 5 min. |
|---|---|---|---|---|---|
| (14) | AEROSIL 200* | 10 | 24 | 40 | 42 |
| (15) | AEROSIL 200* | 20 | 32 | 41 | 42 |
| (16) | AEROSIL R972** | 5 | 48 | 42 | 42 |
| (17) | AEROSIL R972 | 10 | over 200 | 40 | 41 |
| (6) | not used | — | 2 | 41 | 41 |

(Note)
*AEROSIL 200: Hydrophilic silica (BET surface area = 200 ± 25 m$^2$/g), a product of Nippon Aerosil K.K.
** AEROSIL R972: Hydrophobic silica (BET surface area = 120 ± 30 m$^2$/g), a product of Nippon Aerosil K.K.

It has been noted from the results shown in Table 2 that the absorbent resin composition containing ultramicroscopic silica, produced in the process of this invention, had excellent absorbency, and maintained the fluidity for a long period of time even after absorption of moisture.

EXAMPLE 5

Using the powders of the absorbent resin compositions (1) and (3) obtained in Example 1, sanitary napkins were prepared, and their absorbency was measured.

The powders of the absorbent resin compositions (1) and (2) were uniformly dispersed between two sheets of absorbent papers (50 g/cm$^2$). The absorbent papers were pressed by an emboss roll to form the absorbent sheets. Then, the assemblies were prepared by laying an absorbent paper, a fluff pulp, an absorbent sheet, a fluff pulp and an absorbent paper on a polyethylene laminate paper in this sequence, and were cut to a size of 6 cm × 16 cm. The cut assemblies were wholly wrapped with a nonwoven fabric, and their both sides were pressed to form sanitary napkins having a total weight of 6.0 g (hereinafter called sanitary napkins (1) and (2)).

The face to be used of these sanitary napkins was upwardly placed on a known-weight wire netting of 10 mesh. Tap water was poured on it for 5 minutes, and then after inclining the netting for one minute, the napkins were weighed. Again, the water-absorbed napkins after pressing by a pressure of 25 g/cm$^2$ were weighed. The results are shown in Table 3.

For comparison, a napkin (comparative napkin) was prepared in the same manner as above except that in the assembly, an absorbent paper was used instead of the absorbent sheet, and its absorbency was measured. The result is also shown in Table 3.

TABLE 3

| Napkin | Absorbent | Weight after absorption | Weight after pressing |
|---|---|---|---|
| Napkin (1) | Absorption resin composition (1) | 105.2 g | 84.9 g |
| Napkin (2) | Absorbent resin composition (3) | 103.4 g | 84.5 g |
| Comparative napkin | — | 73.6 g | 62.5 g |

It has been found from the results shown in Table 3 that the napkins prepared by using the absorbent resin compositions of this invention have an excellent absorbency and is excellent in a fluid-retaining property under pressure.

We claim:

1. A process for producing an absorbent resin composition, which comprises copolymerizing in aqueous solution a mixture of 100 parts by weight of an acrylate salt monomer (B) composed of 0 to 50 mol% of acrylic acid and 50 to 100 mol% of an alkali metal acrylate and 0.001 to 5 part by weight of a crosslinkable monomer (C) having 2 to 4 groups selected from $CH_2$=CHCO—, $CH_2$=C(CH$_3$)CO— and $CH_2$=CH—CH$_2$— in the molecule in the presence of at least one surface-active agent (A) selected from water-soluble surface-active agents and water-dispersible surface-active agents in the presence of a water-soluble radical polymerization initiator while maintaining the initial concentration of said mixture at 25% by weight to saturation; and drying the resulting gel-like hydrous polymer under heat.

2. The process of claim 1 wherein the surface-active agent (A) is non-ionic surface-active agents of which HLB value is in a range of 7–20.

3. The process of claim 1 wherein the amount used of the surface-active agent (A) is 0.01–10 parts by weight per 100 parts by weight of the acrylate salt monomer (B).

4. The process of claim 1 wherein the alkali metal acrylate is sodium acrylate.

5. The process of claim 1 wherein the acrylate salt monomer (B) is composed of 10–40 mol% of acrylic acid and 60–90 mol% of an alkali metal acrylate.

6. The process of claim 1 wherein the crosslinkable monomer C is at least one member selected from the group consisting of diacrylates and dimethacrylates of ethylene glycol, diethylene glycol, triethylene glycol, propylene glycol, 1,4-butanediol, 1,5-pentanediol, 1,6-hexanediol, neopentyl glycol, trimethylolpropane and pentaerythritol; triacrylates and trimethacrylates of trimethylolpropane and pentaerythritol; tetraacrylate and tetramethacrylate of pentaerythritol; N,N'-methylenebisacrylamide; N,N'-methylenebismethacrylamide; and triallyl isocyanurate.

7. The process of claim 1 wherein the crosslinkable monomer (C) is N,N'-methylenebisacrylamide.

8. The process of claim 1 wherein the crosslinkable monomer (C) is trimethylolpropane triacrylate.

9. The process of claim 1 wherein the drying temperature is in a range of 100°–230° C.

10. A process for producing an absorbent resin composition, which comprises copolymerizing in aqueous solution a mixture of 100 parts by weight of an acrylate salt monomer (B) composed of 0 to 50 mol% of acrylic acid and 50 to 100 mol% of an alkali metal acrylate and 0.001 to 5 part by weight of a crosslinkable monomer (C) having 2 to 4 groups selected from $CH_2=CHCO-$, $CH_2=C(CH_3)CO-$ and $CH_2=CH-CH_2-$ in the molecule in the presence of at least one surface-active agent (A) selected from water-soluble surface-active agents and water-dispersible surface-active agents in the presence of a water-soluble radical polymerization initiator while maintaining the initial concentration of said mixture at 25% by weight to saturation, drying the resulting gel-like hydrous polymer under heat, followed by pulverization, and then blending the resulting resin powder (D) with 0.01 to 10 parts by weight, per 100 parts by weight of the powder, of ultramicroscopic silica (E) having a specific surface area, measured by the Brunauer-Emmett-Teller method, of at least about 50 $m^2/g$ and a particle diameter of not more than about 0.05 micron.

11. The process of claim 10 wherein the surface-active agent (A) is non-ionic surface-active agents of which HLB value is in a range of 7–20.

12. The process of claim 10 wherein the amount used of the surface-active agent (A) is 0.01–10 parts by weight per 100 parts by weight of the acrylate salt monomer (B).

13. The process of claim 10 wherein the alkali metal acrylate is sodium acrylate.

14. The process of claim 10 wherein the acrylate salt monomer (B) is composed of 10–40 mol% of acrylic acid and 60–90 mol% of an alkali metal acrylate.

15. The process of claim 10 wherein the crosslinkable monomer (C) is at least one member selected from the group consisting of diacrylates and dimethacrylates of ethylene glycol, diethylene glycol, triethylene glycol, propylene glycol, 1,4-butanediol, 1,5-pentanediol, 1,6-hexanediol, neopentyl glycol, trimethylolpropane and pentaerythritol; triacrylates and trimethacrylates of trimethylolpropane and pentaerythritol; tetraacrylate and tetramethacrylate of pentaerythritol; N,N'-methylenebisacrylamide; N,N'-methlenebismethacrylamide; and triallyl isocyanurate.

16. The process of claim 10 wherein the crosslinkable monomer (C) is N,N'-methylenebisacrylamide.

17. The process of claim 10 wherein the crosslinkable monomer (C) is trimethylolpropane triacrylate.

18. The process of claim 10 wherein the drying temperature is in a range of 100°–230° C.

* * * * *

UNITED STATES PATENT AND TRADEMARK OFFICE
CERTIFICATE OF CORRECTION

PATENT NO. : 4,286,082
DATED : August 25, 1981
INVENTOR(S) : Tsubakimoto, et al.

It is certified that error appears in the above—identified patent and that said Letters Patent is hereby corrected as shown below:

Page 1, item [73] should read as follows:

Nippon Shokubai Kagaku Kogyo Co., Ltd.

Claim 6, line 2, delete "C" and insert -- (C) --

Signed and Sealed this

Twenty-seventh Day of October 1981

[SEAL]

Attest:

GERALD J. MOSSINGHOFF

Attesting Officer

Commissioner of Patents and Trademarks